US009797836B1

(12) United States Patent
Sinclair et al.

(10) Patent No.: US 9,797,836 B1
(45) Date of Patent: Oct. 24, 2017

(54) HYPERSPECTRAL IMAGING FLOW CYTOMETER

(71) Applicant: Sandia Corporation, Albuquerque, NM (US)

(72) Inventors: Michael B. Sinclair, Albuquerque, NM (US); Howland D. T. Jones, Rio Rancho, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 838 days.

(21) Appl. No.: 13/769,724

(22) Filed: Feb. 18, 2013

Related U.S. Application Data

(60) Provisional application No. 61/604,963, filed on Feb. 29, 2012.

(51) Int. Cl.
*G01N 21/64* (2006.01)
*G01N 21/65* (2006.01)

(52) U.S. Cl.
CPC .................... *G01N 21/64* (2013.01)

(58) Field of Classification Search
CPC ..... B01L 2200/0652; B01L 2200/0668; G01N 2015/149; G01N 15/1459; G01N 15/1463; G01N 15/1475; G01N 2015/1006; G01N 15/1404; G01N 15/147; G01N 21/64; G01N 27/447
USPC ........................................................ 348/135
See application file for complete search history.

(56) References Cited

U.S. PATENT DOCUMENTS

| | | | | |
|---|---|---|---|---|
| 5,444,527 | A * | 8/1995 | Kosaka | 356/73 |
| 8,134,705 | B2 * | 3/2012 | Kaduchak | G01N 15/1404 356/337 |
| 8,830,451 | B1 * | 9/2014 | Graves et al. | 356/73 |
| 2007/0178067 | A1 * | 8/2007 | Maier | G01N 21/65 424/93.2 |
| 2009/0014360 | A1 * | 1/2009 | Toner | B01D 21/0087 209/208 |

OTHER PUBLICATIONS

M.B. Sinclair et al., Design, Construction, Characterization, and Application of a Hyperspectral Microarray Scanner, Applied Optics, vol. 43, No. 10 (2004), pp. 2079-2088.
M.B. Sinclair et al., Hyperspectral Confocal Microscope, Applied optics, vol. 45, No. 24 (2006), pp. 6283-6291.
J.A. Tony Ohlhausen et al., Multivariate Statistical Analysis of Time-of-Flight Secondary Ion Mass Spectrometry Images Using AXSIA, Applied Surface Science 231-232 (2004), pp. 230-234.
Howland D.T. Jones et al., Weighting Hyperspectral Image Data for Improved Multivariate Curve Resolution Results, J. Chemometrics, 22 (2008), pp. 482-490.

(Continued)

*Primary Examiner* — Obafemi Sosanya
(74) *Attorney, Agent, or Firm* — Kevin W. Bieg

(57) ABSTRACT

A hyperspectral imaging flow cytometer can acquire high-resolution hyperspectral images of particles, such as biological cells, flowing through a microfluidic system. The hyperspectral imaging flow cytometer can provide detailed spatial maps of multiple emitting species, cell morphology information, and state of health. An optimized system can image about 20 cells per second. The hyperspectral imaging flow cytometer enables many thousands of cells to be characterized in a single session.

13 Claims, 11 Drawing Sheets

(56) References Cited

OTHER PUBLICATIONS

David M. Haaland et al., Hyperspectral Confocal Fluorescence Imaging: Exploring Alternative Multivariate Curve Resolution Approaches, Applied Spectroscopy, vol. 63, No. 3 (2009), pp. 271-279.

Jerilyn A. Timlin et al., Imaging Multiple Endogenous and Exogenous Fluorescent Species in Cells and Tissues, Proc. of SPIE, vol. 6088 (2006), pp. 608805-1-608805-10.

M. Juanita Martinez, Identification and Removal of Contaminating Fluorescence from Commercial and In-House Printed DNA Microarrays, Nucleic Acids Research, vol. 31, No. 4 (2003), pp. 1-8.

Jerilyn A. Timlin et al., Hyperspectral Microarray Scanning: Impact on the Accuracy and Reliability of Gene Expression Data, BMC Genomics 6:72 (2005), pp. 1-11.

Jerilyn A. Timlin et al., Hyperspectral Imaging of Biological Targets: The Difference a High Resolution Spectral Dimension and Multivariate Analysis Can Make, IEEE International Symposium on Biomedical Imaging (2004), pp. 1529-1532.

Jerilyn A .Timlin et al., Accurate Measurement of Cellular Autofluorescence is Critical for Imaging of Host-Pathogen Interactions, Proc. of SPIE vol. 6859 (2008), pp. 68590A-1-68590A-9.

Ryan W. Davis et al., Accurate Detection of Low Levels of Fluorescence Emission in Autofluorescent Background: Francisella-Infected Macrophage Cells, Microscopy and Microanalysis, 16 (2010), pp. 478-487.

Ryan W. Davis et al., Antimicrobial Peptide Interactions with Silica Bead Supported Bilyaers and *E. coli*: Buforin II, Magainin II, and Arenicin, Journal of Peptide Science, 15 (2009), pp. 511-522.

Wim F.J. Vermaas et al., In Vivo Hyperspectral Confocal Fluorescence imaging to Determine Pigment Localization and Distribution in Cyanobacterial Cells, PNAS, vol. 105, No. 10 (2008), pp. 4050-4055.

Vicki L. Sutherland et al., Advanced Imaging of Multiple mRNAs in Brain Tissue Using a Custom Hyperspectral Imager and Multivariate Curve Resolution, Journal of Neuroscience Methods, 160 (2007), pp. 144-148.

M. Cristina Pedroso et al., Hyperspectral Confocal Fluorescence Microscope: A New Look into the Cell, Microscopy Today.

* cited by examiner

HYPERSPECTRAL IMAGING FLOW CYTOMETER

CROSS-REFERENCE TO RELATED APPLICATION

This application claims the benefit of U.S. Provisional Application No. 61/604,963, filed Feb. 29, 2012, which is incorporated herein by reference.

STATEMENT OF GOVERNMENT INTEREST

This invention was made with Government support under contract no. DE-AC04-94AL85000 awarded by the U. S. Department of Energy to Sandia Corporation. The Government has certain rights in the invention.

FIELD OF THE INVENTION

The present invention relates to flow cytometry and, in particular, to a high throughput hyperspectral imaging flow cytometer.

BACKGROUND OF THE INVENTION

A hyperspectral microarray scanner and a hyperspectral confocal microscope have been developed over the past several years. See M. B. Sinclair et al., *Applied Optics* 43, 2079 (2004); and M. B. Sinclair et al., *Applied Optics* 45, 6283 (2006). In addition, efficient multivariate data analysis algorithms and software have been developed. See J. A. T. Ohlhausen et al., *Applied Surface Science* 231/232, 230 (2004); H. D. T. Jones et al., *J. Chemometrics* 22, 482 (2008); and D. M. Haaland et al., *Appl. Spectrosc.* 63, 271 (2009). Initial application of these hyperspectral technologies to biological investigations has revealed several distinct advantages of the hyperspectral approach, including: improved accuracy for the measurement of low level emissions; the ability to simultaneously monitor many emitting species; the ability to identify and remove unwanted contributions from contaminants; and the ability to identify and utilize (or remove) cell autofluorescence. See J. A. Timlin et al., *Proc. SPIE* 6088, 608805-1 (2006); M. J. Martinez et al., *Nucleic Acids Research* 31, 1 (2003); J. A. Timlin et al., *Bmc Genomics* 6, 72 (2005); J. A. Timlin et al., *IEEE International Symposium on Biomedical Imaging*, 1529 (2004); and J. A. Timlin et al., *Proc. SPIE* 6859, 68590A-1 (2008). More recently, the advantages of these hyperspectral imaging technologies have been clearly demonstrated in a series of detailed biological investigations. See R. W. Davis et al., *Microscopy and Microanalysis* 16, 478 (2010); R. W. Davis et al., *Journal of Peptide Science* 15, 511 (2009); W. F. J. Vermaas et al., *Proceedings of the National Academy of Sciences of the United States of America* 105, 4050 (2008); V. L. Sutherland et al., *Journal of Neuroscience Methods* 160, 144 (2007); and M. C. Pedroso et al., *Microscopy Today* 18, 14 (2010).

During this same time period, the bioscience community has placed increasing emphasis on the development of high throughput instrumentation. The general advantages of increased throughput include the ability to characterize a larger number of compounds, as well as an increase in the reliability and statistical significance of the measurements. Thus, in genomics and proteomics, increased throughput allows for more accurate investigation of a larger number of genes/proteins. Likewise, in drug development, high throughput allows for the screening of large chemical libraries for desired effectiveness. In cytometry, increased throughput allows larger cell populations to be screened and sorted more quickly.

However, a need remains for a high throughput hyperspectral imaging flow cytometer that enables large complex cell populations to be screened and sorted quickly.

SUMMARY OF THE INVENTION

The present invention is directed to a hyperspectral imaging flow cytometer, comprising a microfluidic flow system for focusing a sample of fluorescent particles in a channel, synchronizing the particles to flow single file through an imaging field in the channel, and sorting the particles into separate bins in response to an analysis of an acquired image of each particle; a particle detection system for detecting the passage of a particle in the channel and providing a trigger; a hyperspectral confocal imaging system whose focal plane is located downstream from the particle detector for laterally scanning a focused laser beam across the imaging field and acquiring a hyperspectral image of fluorescence emitted by a particle in the imaging field in response to the trigger; and an analyzer for real-time multivariate analysis of the acquired image of the particle to direct the microfluidic system to sort the particle into a bin. The particle can be any geometric object that can provide a suitable hyperspectral image within the field-of-view of the confocal imaging system, such as a biological cell or fluorescent bead. The flow velocity of the particles in the channel can be greater than 50 μm/sec and up to about 800 μm/sec or greater. Hydrodynamic focusing can be used to focus the sample of particles in the channel. The particle detector is preferably an optical detection system, such as a laser scatterer or machine vision system, that provides the trigger to the imager. The hyperspectral images can be analyzed using multivariate analysis algorithms, such as Classical Least Squares (CLS), Multivariate Curve Resolution (MCR), or Principle Component Analysis (PCA) algorithms, to spatially isolate the emitting species with the images. Both spectral and/or spatial information in the images can be used to sort the particles. Dielectrophoretic sorting or other sorting techniques can be used to sort the particles into separate bins.

For example, the hyperspectral imaging flow cytometer can acquire high-resolution hyperspectral images of cells flowing through the microfluidic system. For example, measurements of algal cells demonstrate that relevant biological information, such as the differentiation of free carotenoids in the lipid bodies from carotenoid bound within the chloroplast can be obtained using hyperspectral imaging flow cytometry. An optimized system can acquire high resolution images at a rate of about 20 cells per second, and can acquire lower resolution images at a proportionately faster rate. While still quite slow compared to traditional non-hyperspectral, non-imaging cytometers, the hyperspectral imaging flow cytometer of the present invention provides vastly richer information about the cells, including detailed spatial maps of multiple emitting species, cell morphology information, and state of health. The hyperspectral imaging flow cytometer enables many thousands of cells to be characterized in a single session, representing a significant breakthrough for high throughput hyperspectral imaging.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Hyperspectral imaging has proven to be of great benefit to biological science due to its ability to provide detailed spatial maps of multiple emitting species and due to its ability to eliminate contributions from unwanted sources, such as autofluorescence. Two hyperspectral imaging systems developed for biological research include the hyperspectral microarray scanner and the hyperspectral confocal microscope. The present invention is directed to a hyperspectral imaging flow cytometer. The hyperspectral imaging flow cytometer shares the hyperspectral advantages of the prior hyperspectral imaging systems, but also allows for the rapid characterization of statistically significant populations. The hyperspectral imaging flow cytometer can be applied to the characterization of cell populations and can be coupled with cell sorting techniques to allow for selection of cells based upon detailed spectral and spatial signatures. In addition, the hyperspectral imaging flow cytometer can be utilized for high throughput bead-based assays in which each bead is highly spatially and spectrally multiplexed for the simultaneous detection of a wide variety of targets. For example, an optimized hyperspectral imaging flow cytometer can be capable of acquiring high resolution images at a rate of about 20 cells per second.

Figure 1:
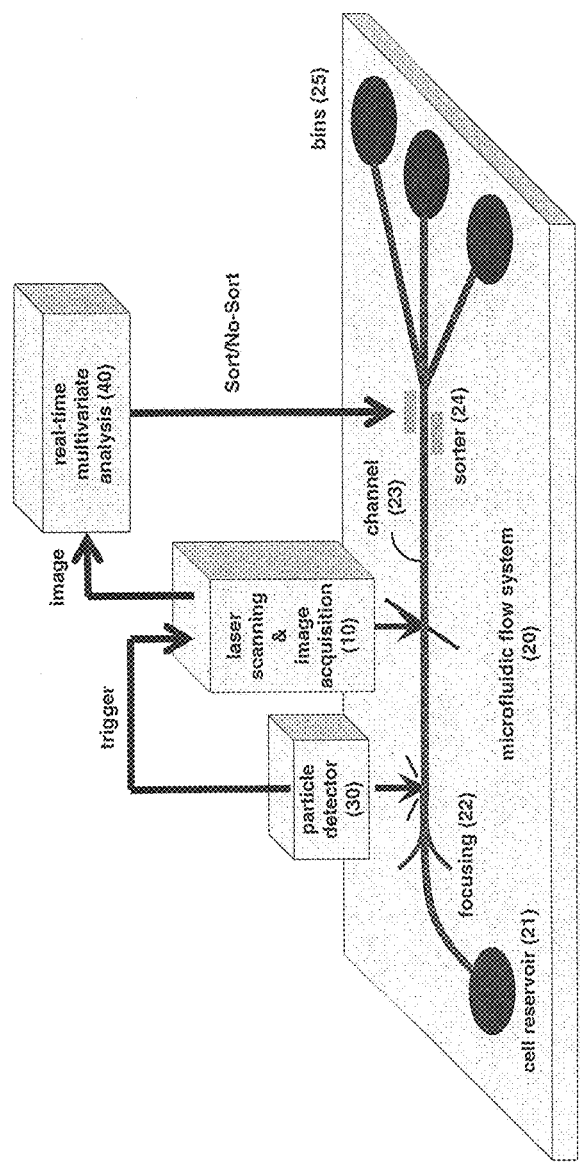
FIG. 1 is a schematic illustration of a hyperspectral imaging flow cytometer system, comprising a microfluidic flow system, a particle detector, a high resolution hyperspectral confocal imager, and an analyzer for real-time multivariate analysis of an acquired image.

FIG. 1 is a schematic illustration of a hyperspectral imaging flow cytometer system of the present invention, comprising a microfluidic flow system 20, a particle detection system 30, a high resolution hyperspectral confocal imaging system 10, and an analyzer 40 for real-time multivariate analysis of an acquired image. The microfluidic flow system 20 extracts particles from a reservoir 21, then focuses 22 and synchronizes the particles into a microfluidic channel 23. The particle detection system 30 can detect the passage of a particle in the channel 23 and trigger the downstream hyperspectral confocal imaging system 10 to scan and acquire a hyperspectral image of the particle as it flows down the channel 23. Real-time multivariate analysis is then performed on the acquired image to discern particle differences and the particles are sorted by a particle sorter 24 into separate bins 25 or discarded as waste.

Figures 2A, 2B:
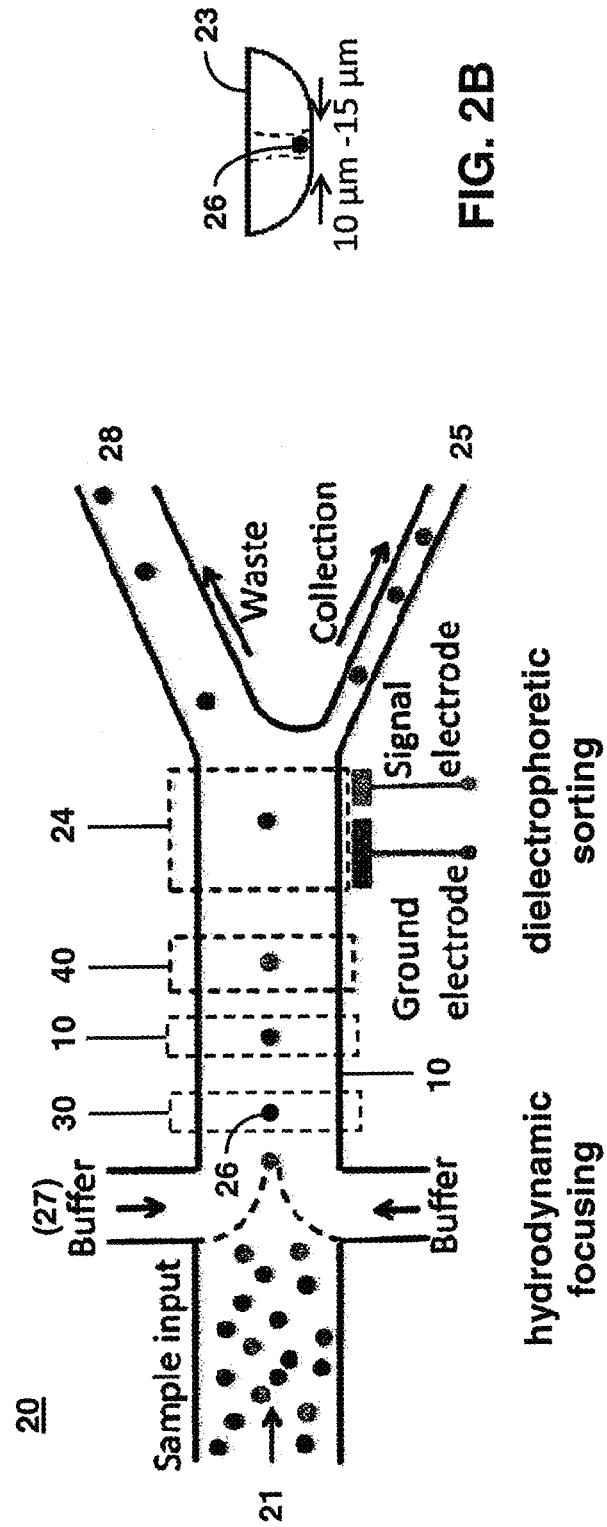
FIG. 2 is a schematic illustration of a microfluidic system for focusing, synchronizing, and sorting cells.

FIG. 2A shows a top-view schematic illustration of an exemplary microfluidic system 20 that can be used to focus and sort cells or similar particles. The microfluidic system lines up cells 26 in single file in a fine stream for interrogation by the imaging system 10. For example, the flow cytometer can use a hydrodynamic focusing system, in which the sample from the cell reservoir 21 is injected into a stream of buffer fluid 27 within the flow channel 23. The sample core remains separate but coaxial within the sheath buffer fluid, enabling the laser beam of the detector 30 to interact and scatter from cells that are focused in a thin-core fluid streamline. For optimal illumination, the cells should be positioned in the center of the laser beam and only one cell should move through the beam at a given moment. In particular, cells are preferably focused fluidically in a uniform plane in the channel to be in optical focus for the imaging system 10. FIG. 2B shows a cross-sectional end view of the channel 23. Cells 26 are preferably focused near the bottom center of the channel 23. This will occur with a Peclet number much greater than 1, such that convective motion dominates diffusion, and a Reynolds number much less than 1, to enable laminar focusing at low flow conditions. Generally, cells will move along the bottom of the channel if the density of the cell is greater than the density of the buffer. Surface grafting (e.g., with polyethylene glycol) can be used to prevent cells from adhering to each other or the channel walls. The optical detection system 30 can be a laser scatterer, machine vision system, or other means that can detect the passage of a cell 26 flowing in the channel 23 and trigger the downstream hyperspectral confocal imaging system 10 to scan and acquire an image of the cell as it flows down the channel. Real-time multivariate analysis can then be performed on the image by the analyzer 40. For example, that multivariate analysis can comprise a HSI (hue, saturation, intensity) analysis of an acquired color image. The HSI analysis can be used to identify biological and morphological cell differences to enable sorting by the sorter 24 into separate bins 25 or discarding as waste 28. For example, since cells have dielectric properties, dielectrophoresis (DEP) can be used to sort the different cells. DEP is a phenomenon in which force is exerted on the dielectric cell when it is subject to a non-uniform electric field, which can be applied by electrodes embedded in the channel. The strength of the DEP force depends on the buffer and cell's electrical properties, on the cell's shape and size, as well as the strength and frequency of the applied electric field. Therefore, the DEP force on a cell can be controlled by the electric field that is applied in response to the image analysis, thereby directing the cells into separate bins depending on the cell differences. Other microfluidic systems can also be used to focus, synchronize, and sort the cells in a sample. See, for example, U.S. Pat. No. 7,713,396 to James et al. and U.S. application Ser. No. 12/481,064 to Ravula et al., both of which are incorporated herein by reference.

Hyperspectral Confocal Microscope Imaging System

Figure 3:
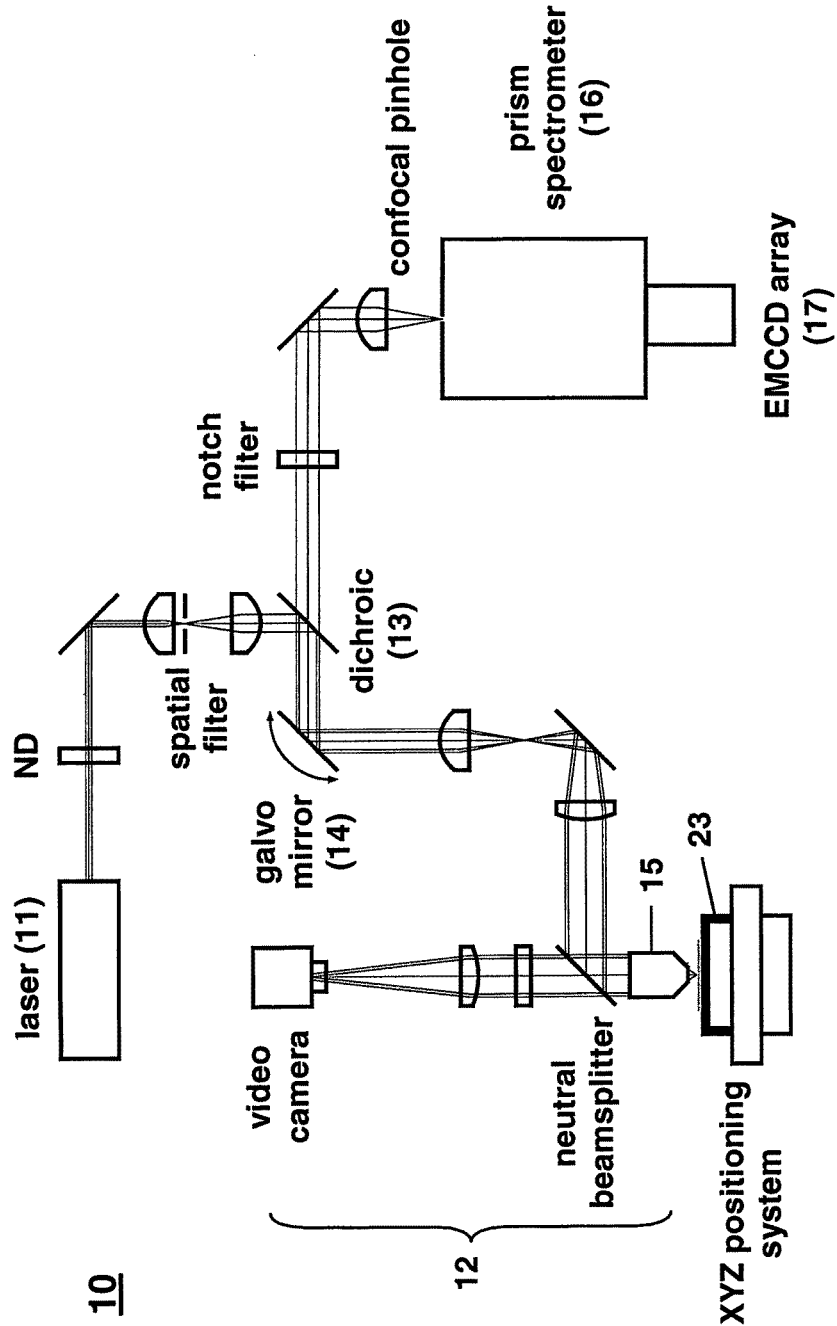
FIG. 3 is a schematic illustration of a hyperspectral confocal microscope that was adapted for use in the hyperspectral imaging flow cytometer.

FIG. 3 shows an exemplary high resolution hyperspectral confocal imaging system 10. The imaging system 10 is based on a hyperspectral confocal microscope. See M. B. Sinclair et al., *Applied Optics* 45, 6283 (2006), which is incorporated herein by reference. Briefly, the excitation source for the exemplary microscope can be a 488 nm laser 11 which injects a laser beam into the microscope 12 via a dichroic filter 13. A galvanometer driven mirror 14 scans the angle of the laser beam as it enters the back aperture of the microscope objective 15. This results in a lateral scanning of the focused laser spot at the focal plane of the objective 15. Fluorescence emitted by a cell in the channel 23 at the focal plane is collected by the objective 15 and directed back through the optical system where it is descanned by the galvanometer driven mirror 14. The fluorescent photons then pass through the dichroic filter 13 and are focused onto the entrance pinhole of a prism spectrometer 16. The prism disperses the fluorescence and projects a dispersed image of the entrance pinhole on the electron multiplying CCD (EM-CCD) detector 17. Row-to-row transfer of the photoelectrons generated by the absorption of the fluorescent photons is synchronized with the scanning of the laser spot on the specimen. The scanning of the mirror and the acquisition of image data from the EMCCD detector are under computer control. The lateral scanning of the focused laser spot can also synchronized with the flow velocity in the microfluidic channel to ensure that a unit aspect ratio image is obtained.

Figure 4:
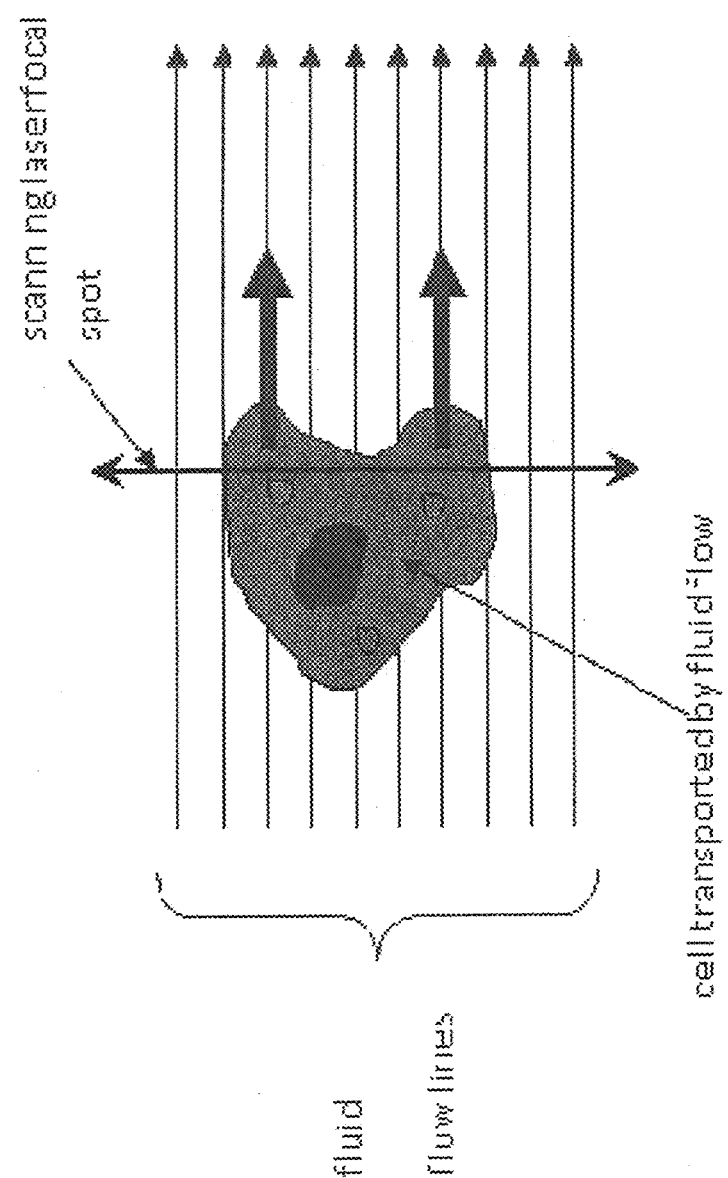
FIG. 4 is a schematic illustration of the basic imaging principle of the hyperspectral imaging flow cytometer.

The primary difference between a hyperspectral confocal microscope and the hyperspectral confocal imaging system of the present invention relates to how the particle is scanned in the direction perpendicular to the scan direction of the laser spot. For the hyperspectral confocal microscope, this scanning is achieved through the use of a computer controlled translation stage, while for the hyperspectral confocal imager, the liquid flow in the microchannel transports the cell past the scanning laser spot, as shown in FIG. 4. Thus the velocity of fluid flow will determine the horizontal pixel resolution as well as the total time required to scan the sample. The optimal flow velocity for unit aspect ratio imaging occurs when the distance traveled during the laser scan retrace time is equal to the pixel-to-pixel spacing in the direction of the laser scan. Therefore, the maximum flow rate that can be utilized with this system is dictated by the readout rate of the EMCCD detector. For example, the detector employed on the exemplary hyperspectral confocal imaging system described below acquired spectra at a maximum rate of ~8300 spectra per second which limits the maximum flow velocity in the microfluidic channel to less than 100 μm per second if reasonable resolution images are to be acquired. This is not a fundamental limitation, however, and newer EMCCD detectors are available with read out rates approaching 64,000 spectra per second.

Figure 5:
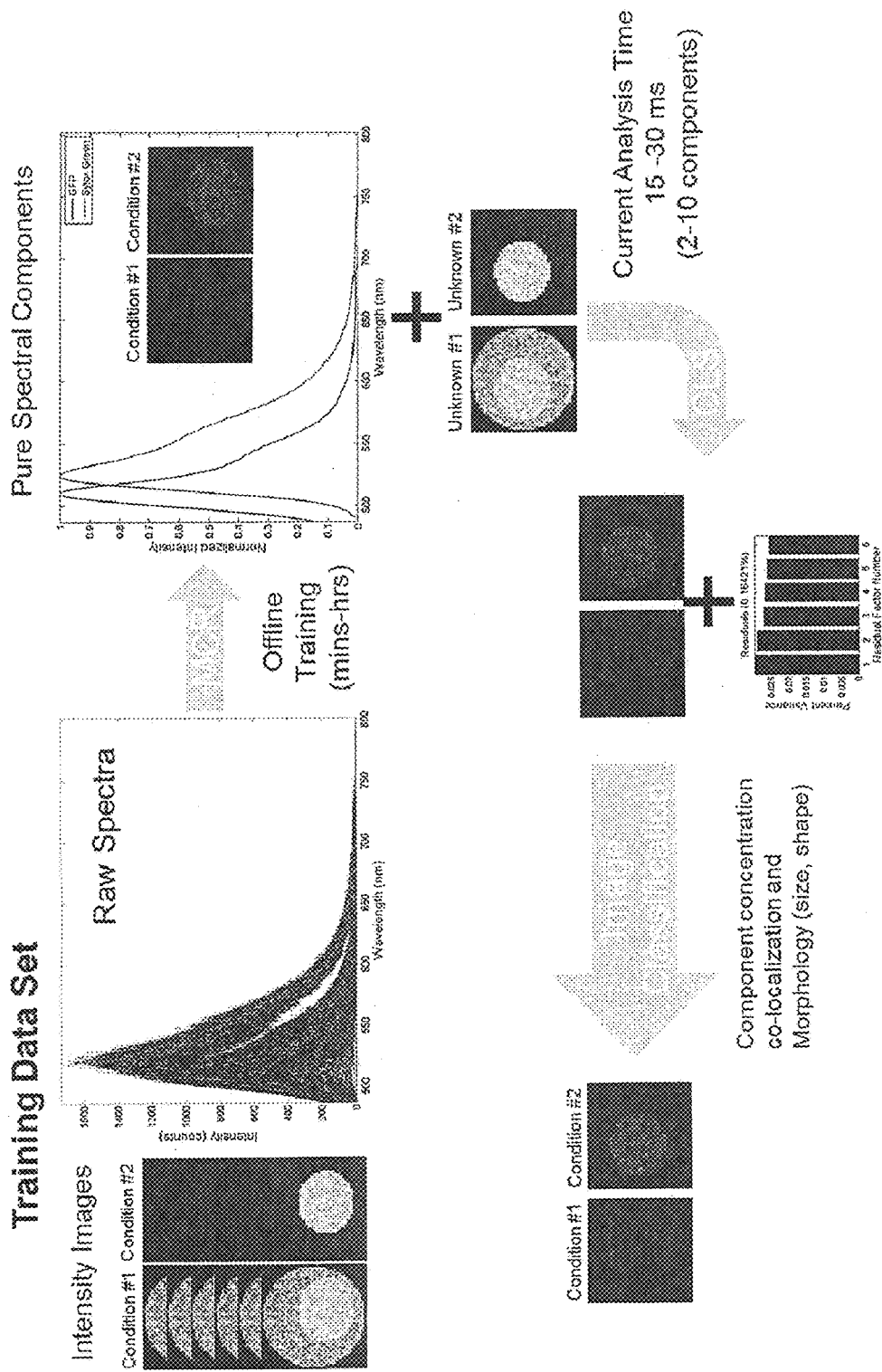
FIG. 5 is a diagram of steps to perform a real-time multivariate analysis on the image to discern biological and morphological cell differences.

FIG. 5 shows steps that can be performed by the analyzer 40 using multivariate analysis techniques to discern biological and morphological cell differences in the hyperspectral image data. Prior to the sorting process of the hyperspectral imaging flow cytometer, Multivariate Curve Resolution (MCR) can be used to extract the pure spectral components from training sample sets. MCR has proven to be a powerful analysis tool for hyperspectral imaging and attaining quantitative data on many known and unknown biological samples. MCR discovers all independently varying species (spectral pure components) present in an image, even those in which there is no a priori information, and provides a relative quantitative analysis of the hyperspectral image data without the need for standards. Although the MCR algorithms are very fast, the primary purpose of MCR is to discover and characterize the sample training sets, so that faster less complex algorithms, such as Classical Least Squares (CLS), can provide rapid real-time sorting decisions. CLS can use the pure spectral components discovered by the MCR characterization process. By projecting these spectral components onto the preprocessed image data generated during the sorting process, CLS can generate quantitative images for each spectral component. Spectral residuals can determine the overall quality or fit of the CLS-modeled data. If the fit is poor or shows extra unmodeled components, two approaches can be taken: 1) exclude the cell image data, especially if this is the result of debris within the image, or 2) augment the CLS model to include new spectral components or exclude existing spectral components from future analyses and experiments. These quantitative images can provide detailed information about the spatial location and co-location of the fluorescence species within cells. This information can then be used in two different modes: 1) to develop detailed statistical information about the quantitative make-up of fluorescence species within a large population of cells, or 2) to use the quantitative information to sort cells based upon desired characteristics to separate a subpopulation of cells for further biological investigations. The first mode does not necessarily require real-time analysis of the image data. There are a number of parameters that can affect the analysis speed that can also affect the ability to do real-time sorting of cells or other particles, for example: image size, number of wavelengths, number of spectral components, and the amount of necessary preprocessing required prior to the analysis. All of these parameters can be adjusted depending on the sensitivity needed for the sorting, which either can increase or decrease the analysis time. Furthermore, any additional characterization steps based upon using the quantitative images, such as determining the co-location of spectral components within the biological cells or using cell morphology for classification, can affect the sorting speed. Using multiple processors on the PC to implement parallel processing capabilities maximizes the efficiency of the algorithms to provide real-time classification of cells and rapid sorting capabilities.

Exemplary Hyperspectral Imaging Flow Cytometer

An exemplary hyperspectral imaging flow cytometer was constructed and tested using fluorescently tagged microspheres, as well as algal cells. Fluorescent specimens, including dye labeled beads and algal cells (*Chlamydomonas Reinhardtti*), were injected into a microfluidic flow system and transported past the imaging field of the previously described hyperspectral confocal microscope. The hyperspectral imaging flow cytometer recorded detailed hyperspectral images showing interesting biological features, such as the localization of free carotenoids in lipid bodies within the algal cells. Such information, obtained for a statistically significant population of algal cells, can be of enormous interest to biologists seeking to understand the mechanisms of lipid production in algae. Testing of the exemplary hyperspectral imaging flow cytometer system also enabled the notional design of an optimized system that can provide high-resolution hyperspectral images at a sustained rate of about 20 cells per second. Such a rate allows many thousands of cells to be characterized per session and represents a significant breakthrough for high throughput hyperspectral imaging.

Microfluidic Flow System

The exemplary microfluidic flow system utilized square channel capillary tubing to transport the test specimens from a storage reservoir to the imaging field. A pressure manifold was constructed to apply variable low pressure to the storage reservoir. Once the pressure is applied, fluid and specimens are forced into the capillary tubing. The pressure required to achieve the required flow velocities (~50 μm/s) can be estimated using Poiseuille's equation and lies in the 0.1-1.0 PSI range. The storage reservoir was fabricated from a small vial whose cap was modified to allow for the application of low pressures to the vial. The cap was also modified by attaching a leur-lock fitting to facilitate connection to the capillary tube. The capillary tubing was fitted to a mating luer-lock fitting using a capillary fitting. A small stir bar was placed inside the storage reservoir and a stir plate was placed under the storage reservoir to provide agitation to keep the specimens from depositing on the bottom of the vial.

To adapt the microfluidic system to the hyperspectral confocal microscope, the protective polyimide coating of the capillary tubing was removed over a ~2 cm section of the tubing. This section of the tubing was then adhered to a standard microscope slide with two of the flat faces of the square tubing perpendicular to the plane of the microscope slide. In this fashion the flat face of the tubing was aligned perpendicular to the optical axis of the microscope objective and high quality imagery could be obtained.

Test Results: Fluorescent Beads

Figure 6:
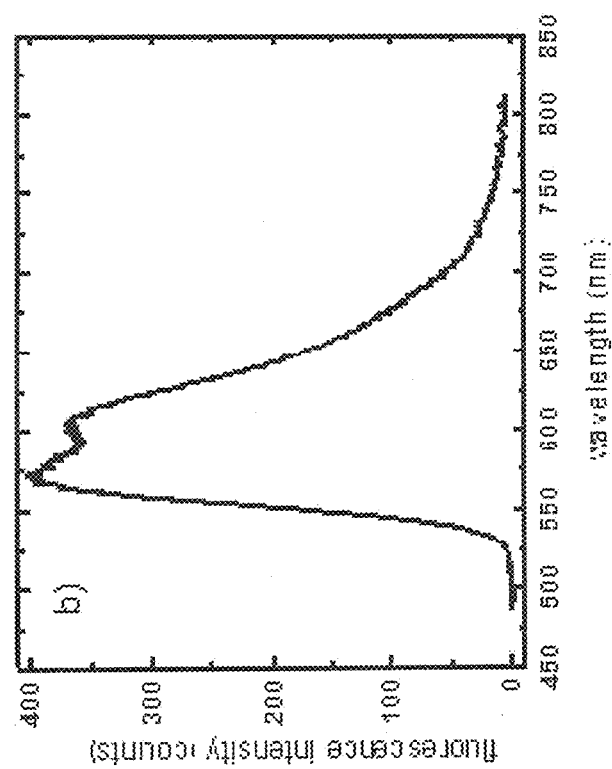
FIG. 6(a) is a hyperspectral image of a 10 μm polystyrene bead.
FIG. 6(b) is a hyperspectral emission spectrum extracted from the image cube, showing the emission spectrum of the fluorescent tag Envy Green.
Figure 6:
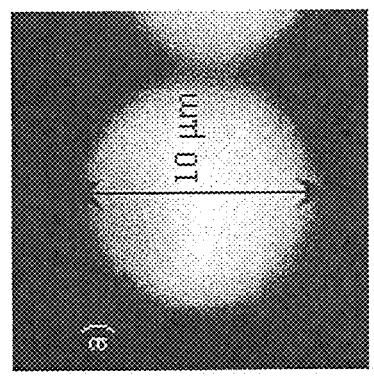

Initial testing of the hyperspectral imaging flow cytometer was performed using commercially available fluorescent microspheres from Bangs Laboratories. The microspheres had a diameter of 9.85 μm and were labeled with the fluorescent compound Envy Green. The absorption maximum (525 nm) and emission maximum (565 nm) of this label are fairly well matched to the spectral detection range of the exemplary hyperspectral imaging flow cytometer. The microspheres were diluted in filtered water and placed in the storage reservoir. FIG. 6(a) shows a hyperspectral image of one of the microspheres obtained using the hyperspectral confocal microscope and FIG. 6(b) shows the emission spectrum from the hyperspectral image.

Figure 7:
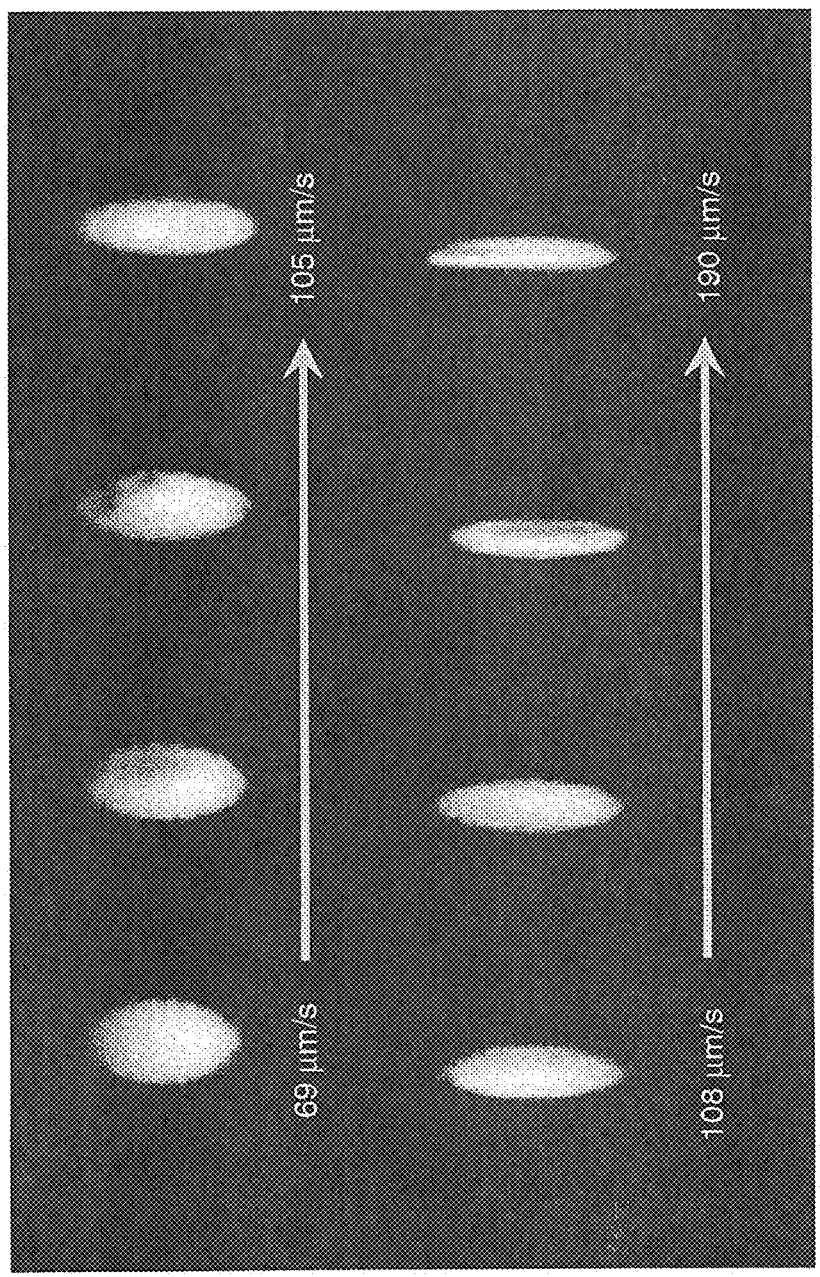
FIG. 7 is montage of hyperspectral images of beads obtained using the hyperspectral imaging flow cytometer.

To obtain hyperspectral images of the fluorescent beads as they moved past the imaging field, a wide field camera was used to detect the arrival of a bead at a location upstream from the imaging region and the acquisition of the hyperspectral image was initiated shortly thereafter. Due to the limitations of the rudimentary microfluidic flow system that was assembled for this exemplary system, precise regulation of the flow velocity was not possible. The flow rate was controlled manually and adjusted over a range that was close to, but somewhat above, the optimal flow velocity for unit aspect ratio imaging. The impact of the higher flow velocity on the obtained hyperspectral images was an increase in the pixel spacing in the direction parallel to the flow velocity. This results in an apparent compression of the bead image along the flow direction which can be utilized to estimate the velocity of the beads as they transited the imaging region. FIG. 7 shows a sequence of hyperspectral images obtained using the hyperspectral imaging flow cytometer of the fluorescent beads moving with a range of velocities. The upper left image was obtained at a flow velocity of approximately 69 um/s which is roughly twice the optimal velocity. Thus this bead image is compressed by a factor of two along the flow direction. As indicated by the progression of images towards the lower right of this figure, the degree of compression increases with the flow velocity. Precise control of the flow velocity is desirable to obtain the highest possible image quality from an optimized hyperspectral imaging flow cytometer.

The images presented in FIG. 7 are extracted from full hyperspectral image cubes and contain detailed information about the emission spectrum (such as is shown in FIG. 6(b)) for each pixel of the image. In addition, substructure was clearly resolved in several of the bead images shown in the upper panel of FIG. 7.

Test Results: Algal Cells

Although the results obtained from the hyperspectral imaging flow cytometer using the fluorescent beads were highly encouraging, the beads only contain a single emitting species, and do not possess any substantial substructure. To more fully characterize the hyperspectral imaging flow cytometer, measurements were performed using the algal cells (*Chlamydomonas Reinhardtii*). These cells contain substantial amounts of chlorophyll-a and chlorophyll-b containing protein complexes which are largely spatially overlapped, and whose emission spectra are highly spectrally overlapped. In addition, the cells contain carotenoids which can be identified through their distinct resonance enhanced Raman emission peaks. Two sets of measurements were performed to allow for optimal observation of the chlorophyll and carotenoid species.

Figure 8:
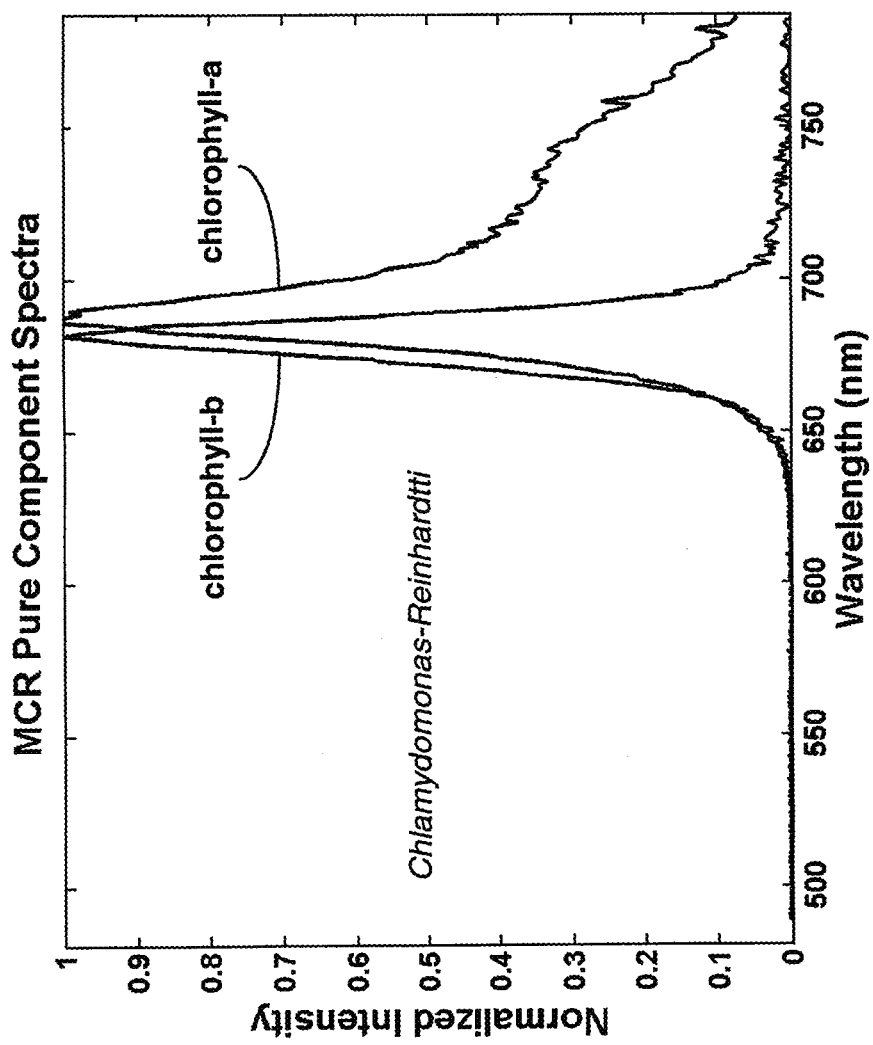
FIG. 8 shows chlorophyll-a and chlorophyll-b pure component spectra obtained using MCR analysis of hyperspectral imaging flow cytometer images of *Chlamydomonas-Reinhardtii*.
Figure 9:
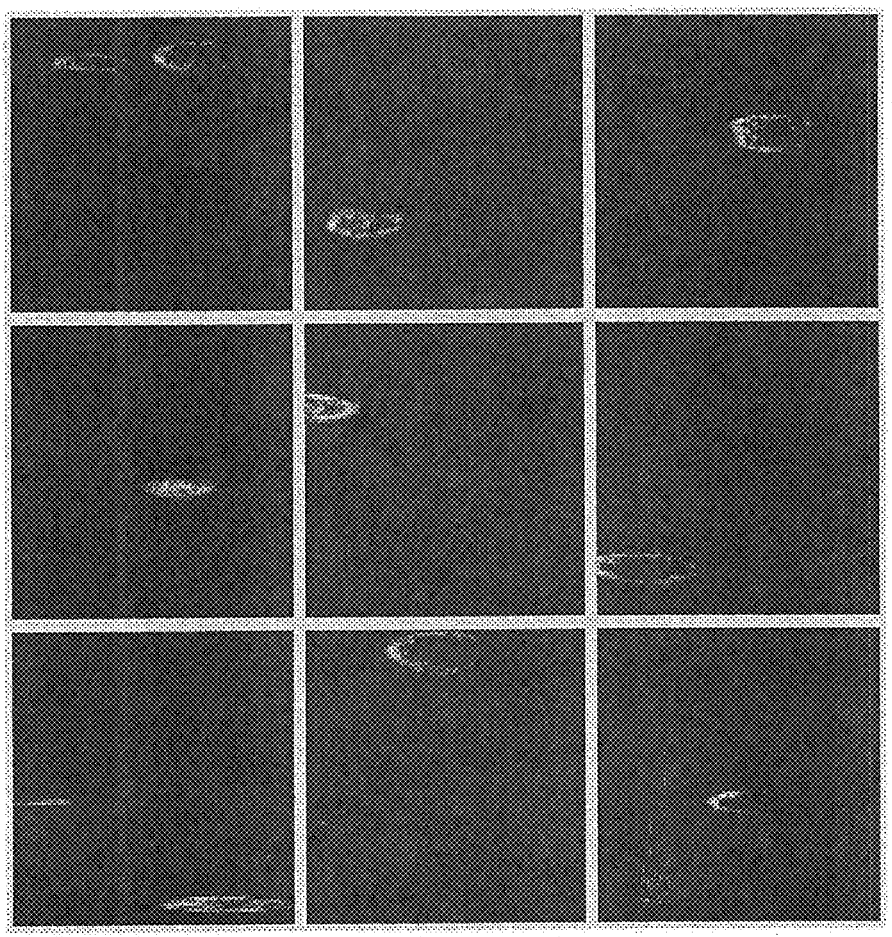
FIG. 9 shows concentration maps of the *Chlamydomonas-Reinhardtii* cells obtained from the MCR analysis of hyperspectral images from the hyperspectral imaging flow cytometer.

To characterize the chlorophyll-a and chlorophyll-b distributions, the exemplary hyperspectral imaging flow cytometer was operated in its normal mode, and the acquired hyperspectral images were analyzed using multivariate curve resolution (MCR) algorithms. FIG. 8 shows the pure component spectra for chlorophyll-a and chlorophyll-b obtained from the MCR algorithm. There is strong overlap of the emission spectra of these two species—filter-based instruments would not be capable of distinguishing these species. FIG. 9 shows the concentration maps for chlorophyll-a and chlorophyll-b emitting species obtained from the MCR algorithm for a number of hyperspectral images obtained using the hyperspectral imaging flow cytometer. As was the case in the fluorescent bead images, there is some compression of the hyperspectral images in the flow direction due to improperly matched flow velocities. Nevertheless, it is clear that high quality images can be obtained using the hyperspectral imaging flow cytometer. Color maps of these images show clearly resolved regions where the chlorophyll-a/chlorophyll-b varies from the average value. Thus, complex spatially and spectrally overlapping emissions can be disentangled from cytometer derived data.

Figure 10:
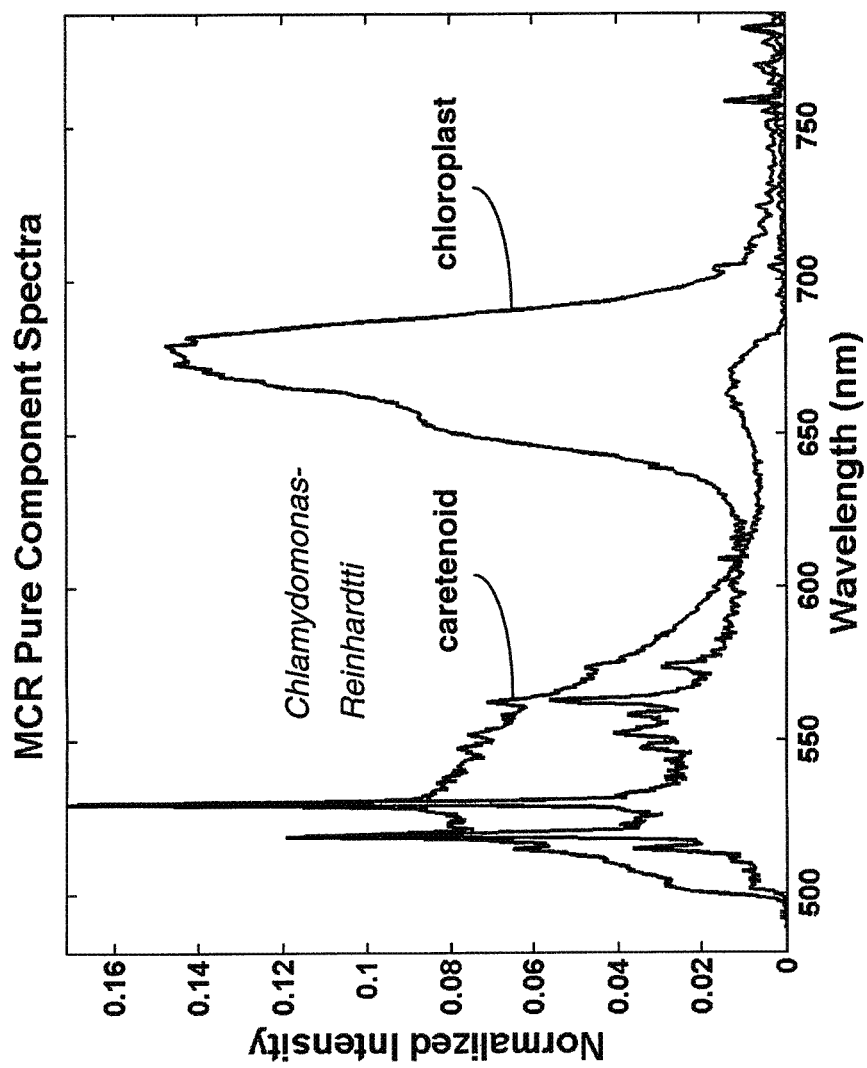
FIG. 10 shows the pure component spectra of free and bound carotenoid obtained using MCR analysis of hyperspectral imaging flow cytometer images of *Chlamydomonas-Reinhardtii*.
Figure 11:
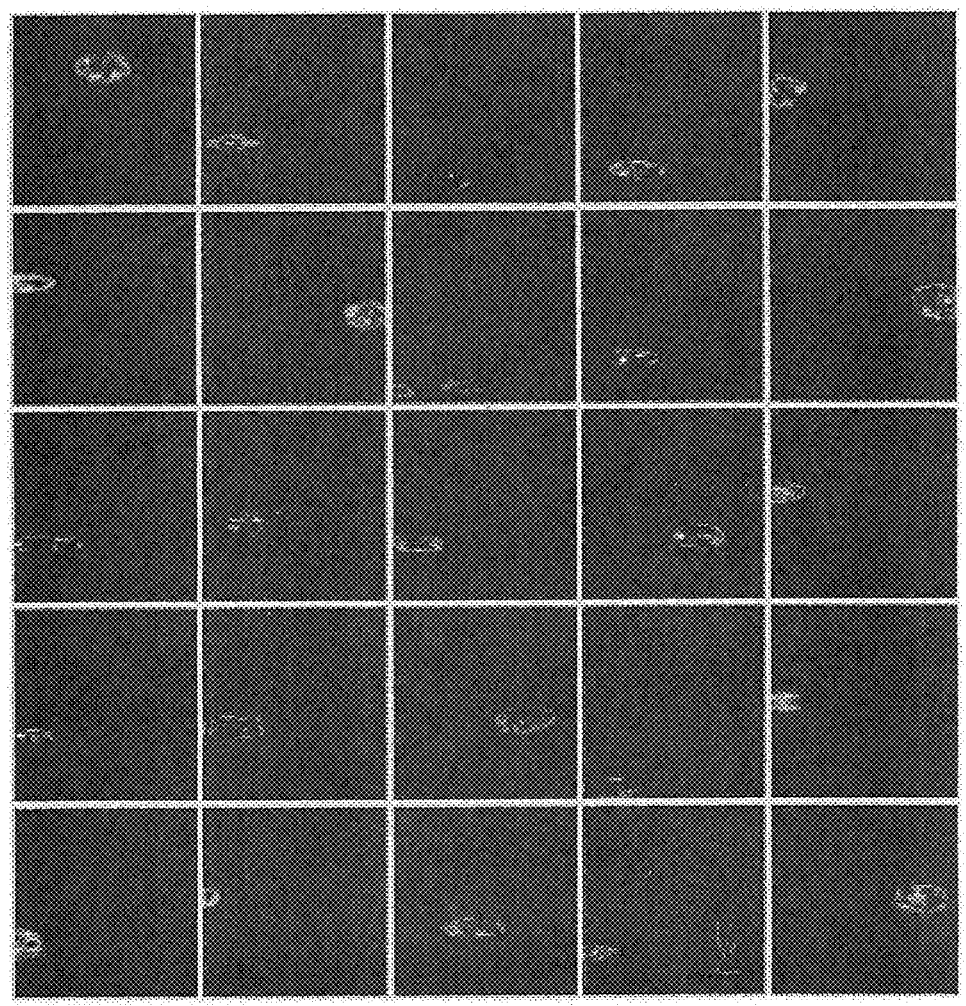
FIG. 11 shows concentration maps of the free carotenoid in lipid and bound carotenoid species (chloroplast) within *Chlamydomonas-Reinhardtii* cells obtained from the MCR analysis of hyperspectral images from the hyperspectral imaging flow cytometer.

A more compelling demonstration of the utility of the hyperspectral imaging flow cytometer was obtained from a second set of measurements which focused on observing the carotenoid species contained in the algal cells. For these measurements a cyan filter was placed in the emission path which attenuated the chlorophyll emission and allowed for greater laser power to be applied so the weak carotenoid emission can be more clearly observed. FIG. 10 shows the MCR-derived pure component spectra for chloroplast-bound carotenoid as well as free carotenoid which tends to be localized in lipid bodies. Each of these spectra exhibit sharp resonance Raman spectral lines which clearly distinguish carotenoid species. In addition, the chloroplast-bound carotenoid contains a broader chlorophyll-like emission band at longer wavelengths. FIG. 11 shows concentration maps of the free and bound carotenoid species within *Chlamydomonas-Reinhardtti* cells obtained from the MCR analysis of hyperspectral images from the hyperspectral imaging flow cytometer. The color images of these carotenoid concentration maps clearly show the localization of free carotenoid in the lipid bodies. Such information is of great biological relevance in assessing the characteristics of algae species and strains for biofuel production.

Optimized Hyperspectral Imaging Flow Cytometer

Based upon the test results presented above, the hyperspectral imaging flow cytometer of the present invention can be of great benefit to biological research. The exemplary system can be further optimized using currently available commercial components, as described below.

Speed of Detection:

To improve the speed of detection, the EMCCD detector used in the exemplary system, which was capable of acquiring ~8300 spectra per second, can be replaced with a smaller pixel count (128×128) EMCCD detector which is capable of recording ~64,000 spectra per second. In addition, the field-of-view and pixel resolution can be reduced from 50 μm and 100×100 pixels per cell in the exemplary system to the smallest possible values that are consistent with the overall cell size and desired pixel resolution. For the algal cells measured herein, a 20 μm field-of-view with a 0.5 μm pixel resolution can provide a 40×40 image and an increase in cell imaging speed of ~6. Combining the two improvements provides an overall throughput increase of approximately 50, with the per-cell imaging time decreased to approximately 25 ms. Assuming an equivalent dead time between before the arrival of adjacent cells, an overall cell imaging rate of 20 cells per second can be achieved. For such a readout speed, the optimal fluid flow velocity would be approximately 800 μm per second which would be much easier to realize than the extremely low flow velocities required in the exemplary system.

Laser Scanning:

The readout rate of the exemplary system corresponds to an 80 Hz retrace rate which is readily achievable using galvanometer driven mirrors. For the faster detection rate system described above, the retrace rate would increase to 1600 Hz. Such a rate might be too large for galvanometer driven mirrors, but is readily achievable using polygon scanning mirrors.

Readout Triggering:

Increasing the readout speed to 20 cells per second requires precise timing of the detector readout. There are several ways this can be achieved. In one approach, the output of the 30 Hz frame rate wide field camera can be analyzed to detect the presence of an incoming cell upstream from the imaging region. After a programmed delay dependent upon the flow velocity, the readout of the EMCCD detector can be initiated. The second approach utilizes a second laser (the trigger laser) which is focused at a location upstream from the imaging region. The light scattered by a cell as it transverses the trigger laser focal spot can be detected and the readout of the EMCCD can be triggered after an appropriate delay.

Microfluidic Flow System:

An optimized hyperspectral imaging flow cytometer requires that substantial attention be paid to the flow system. First, the flow velocity should stable, and adjustable over a reasonable range to accommodate different readout rates. Next, the upper window of the imaging region of the flow channel should be compatible with high quality microscope objectives—it should be flat and approximately the same thickness as a cover slip (~170 μm). In addition, the flow system should be constructed using filters and other microfluidic techniques to prevent clogging of the flow channels. Finally, the use of sheathing flows to force the cells to move along the center of the channel is desirable.

Real-Time Multivariate Analysis:

Acquisition of hyperspectral cell images at a rate of 20 cells per second places significant demands on the multivariate analysis algorithms. Real-time analysis of the images is feasible through the utilization of parallel processes on a multi-processor computer. One process/processor can be responsible for controlling the hardware system and streaming the hyperspectral image data to memory. Message passing protocols can then be used to notify the analysis process of the availability of new image data. If necessary, high performance Graphics Processing Units (GPUs) can also be employed for real-time analysis. The analysis process can be based upon classical least squares projection using pure component spectra obtained by measuring a small set of "training data". In this fashion, only the processed concentration maps and pure component spectra need be saved rather than the large volume of raw data. Further analysis algorithms can then be used to obtain desired biological information, such as state-of-health, cell-morphology, or species co-localization.

The present invention has been described as a hyperspectral imaging flow cytometer. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A hyperspectral imaging flow cytometer, comprising:
 a microfluidic flow system for focusing a sample of fluorescent particles in a channel, synchronizing the particles to flow single file through an imaging field in the channel, and sorting the particles into separate bins in response to an analysis of an acquired image of each particle;
 a particle detection system for detecting the passage of a particle in the channel and providing a trigger;
 a hyperspectral confocal imaging system having a focal plane downstream from the particle detection system for laterally scanning a focused laser beam across the imaging field and acquiring a hyperspectral image of fluorescence emitted by a particle in the imaging field in response to the trigger; and
 an analyzer for real-time multivariate analysis of the acquired hyperspectral image of the particle to direct the microfluidic system to sort the particle into a bin.

2. The hyperspectral imaging flow cytometer of claim 1, wherein the particles comprise biological cells.

3. The hyperspectral imaging flow cytometer of claim 1, wherein the particles comprise fluorescently tagged beads.

4. The hyperspectral imaging flow cytometer of claim 1, wherein the particles comprise at least two emitting species.

5. The hyperspectral imaging flow cytometer of claim 1, wherein the flow velocity of the particles in the channel is greater than 50 μm/sec.

6. The hyperspectral imaging flow cytometer of claim 1, wherein the focusing a sample of particles in a channel comprises hydrodynamic focusing.

7. The hyperspectral imaging flow cytometer of claim 1, wherein the particle detection system comprises a laser scatterer or machine vision system.

8. The hyperspectral imaging flow cytometer of claim 1, wherein the field-of-view of the confocal imaging system is less than 50 μm.

9. The hyperspectral imaging flow cytometer of claim 1, wherein the confocal imaging system acquires hyperspectral images at a rate of approximately 20 particles per second or greater.

10. The hyperspectral imaging flow cytometer of claim 1, wherein the multivariate analysis comprises Classical Least Squares, Multivariate Curve Resolution, or Principle Component Analysis.

11. The hyperspectral imaging flow cytometer of claim 1, wherein the particle is sorted using the spectral information from the multivariate analysis of the acquired hyperspectral image of the particle.

12. The hyperspectral imaging flow cytometer of claim 1, wherein the particle is sorted using the spatial information from the multivariate analysis of the acquired hyperspectral image of the particle.

13. The hyperspectral imaging flow cytometer of claim 1, wherein the sorting the particles into separate bins comprises dielectrophoretic sorting.

\* \* \* \* \*